United States Patent
Liu et al.

(10) Patent No.: US 12,398,388 B2
(45) Date of Patent: Aug. 26, 2025

(54) AGGREGATE OF CELL CARRIER PARTICLES AND METHOD FOR PREPARING SAME

(71) Applicant: Beijing CytoNiche Biotechnology Co., Ltd., Beijing (CN)

(72) Inventors: Wei Liu, Beijing (CN); Xiaojun Yan, Beijing (CN)

(73) Assignee: Beijing CytoNiche Biotechnology Co., Ltd., Beijing (CN)

( * ) Notice: Subject to any disclaimer, the term of this patent is extended or adjusted under 35 U.S.C. 154(b) by 833 days.

(21) Appl. No.: 17/303,130

(22) Filed: May 20, 2021

(65) Prior Publication Data

US 2021/0277380 A1 Sep. 9, 2021

Related U.S. Application Data

(63) Continuation-in-part of application No. PCT/CN2019/090848, filed on Jun. 12, 2019.

(51) Int. Cl.
| | | |
|---|---|---|
| *C12N 11/02* | (2006.01) | |
| *B29B 11/06* | (2006.01) | |
| *B29C 41/00* | (2006.01) | |
| *B29C 41/38* | (2006.01) | |

(52) U.S. Cl.
CPC ............. *C12N 11/02* (2013.01); *B29B 11/06* (2013.01); *B29C 41/003* (2013.01); *B29C 41/38* (2013.01); *B29K 2089/00* (2013.01); *B29K 2833/12* (2013.01)

(58) Field of Classification Search
CPC ....... C12N 11/02; B29B 11/06; B29C 41/003; B29C 41/38; B29K 2089/00; B29K 2833/12
See application file for complete search history.

(56) References Cited

U.S. PATENT DOCUMENTS

| | | |
|---|---|---|
| 5,869,321 A | 2/1999 | Franklin |
| 6,068,855 A | 5/2000 | Leslie et al. |
| 7,531,334 B2 | 5/2009 | Cheng et al. |
| 8,597,686 B2 | 12/2013 | Yamasaki et al. |

(Continued)

FOREIGN PATENT DOCUMENTS

| | | |
|---|---|---|
| CN | 102099462 A | 6/2011 |
| CN | 102250390 A | 11/2011 |

(Continued)

OTHER PUBLICATIONS

English translation of JP 2014218464 (Year: 2014).*

(Continued)

*Primary Examiner* — Catherine S Branch
*Assistant Examiner* — Andrea Wu
(74) *Attorney, Agent, or Firm* — Ingrassia Fisher & Lorenz, LLP

(57) ABSTRACT

The present disclosure discloses an aggregate of cell carrier particles and a method for preparing same. The aggregate of cell carrier particles is formed by aggregating cell carrier particles and has a particular shape including the shape of a tablet and the shape of a block. The method for preparing the aggregate of cell carrier particles is a punch-forming process, a mold-forming process, a lyophilization process or a dehydrating-evaporating process.

12 Claims, 10 Drawing Sheets

(56) References Cited

U.S. PATENT DOCUMENTS

2007/0243607 A1  10/2007  Cheng et al.
2011/0165671 A1   7/2011  Halter et al.
2018/0291326 A1  10/2018  Lundgren et al.

FOREIGN PATENT DOCUMENTS

| CN | 105462915 A | 4/2016 |
| CN | 109762802 A | 5/2019 |
| JP | 2014218464 A | 11/2014 |
| JP | 2017169560 A | 9/2017 |
| WO | 2005010162 A2 | 2/2005 |
| WO | 2006106889 A1 | 10/2006 |
| WO | 2008118416 A1 | 10/2008 |

OTHER PUBLICATIONS

CNIPA, International Search Report issued in IA No. PCT/CN2019/090848, dated Nov. 1, 2019.

Wang, S. et al. "Vero Cells Cultured with Microcarrier System to Produce High Titer Rabies Virus Solution", Chinese Journal of Biologicals, Nov. 30, 2004, pp. 380 and 203, vol. 17, No. 6.

Kornmuller, A. et al. "Fabrication of Extracellular Matrix-derived Foams and Microcarriers as Tissue-specific Cell Culture and Delivery Platforms", Journal of Visualized Experiments, Apr. 11, 2017 (Apr. 11, 2017), No. 122.

EPO, European Extended Search Report issued in EP Appl. No. 19913881.9, dated Oct. 31, 2022.

\* cited by examiner

AGGREGATE OF CELL CARRIER PARTICLES AND METHOD FOR PREPARING SAME

CROSS-REFERENCE TO RELATED APPLICATIONS

This application is a Continuation-in-part of International Application No. PCT/CN2019/090848, filed Jun. 12, 2019, which was published under PCT Article 21(2) and which claims priority to Chinese Application No. 201910079680.3, filed Jan. 28, 2019, which are all hereby incorporated in their entirety by reference.

TECHNICAL FIELD

The present disclosure relates to an aggregate of cell carrier particles and a method for preparing same.

BACKGROUND

Cell carrier particles (typically 1-1000 um in diameter) refer to microbeads that can be used in the growth or co-culture of adherent cells. Currently, all the commercially available microcarriers are used, stored and packaged in a powdery form. However, since microcarriers are micron-scale microbeads, they are prone to generate a large amount of static electricity in a dry powder state. Therefore, during use or transportation, it would easily cause spillage of microcarrier powder, reduction in the effective mass, as well as pollution of the surrounding environment and the product per se. It is also difficult to store these powdery microcarriers, because their own nature leads to such a limitation that no matter what kind of package is utilized, it would still result in a large amount of unnecessary loss. Moreover, it is also difficult to use them, as a lot of measuring instruments are needed as auxiliary tools in many procedures such as weighing, which is very time-consuming and effort-consuming. Therefore, there is a need to provide an aggregate of cell carrier particles, so as to facilitate its use in cell culture. In addition, other objects, desirable features and characteristics will become apparent from the subsequent summary and detailed description, and the appended claims, taken in conjunction with the accompanying drawings and this background.

SUMMARY

The object of the present disclosure is to provide an aggregate of cell carrier particles and a method for preparing same. In the present disclosure, the cell carrier particles in a powder state are aggregated and shaped to form an aggregate. The aggregate avoids the problems caused by a microcarrier powder during use, packaging, and transportation, such as the generation of a large amount of static electricity, being easy to spill during use and weighing, the electrostatic adsorption on the wall of a container or an operating tool, the difficulty in operation, causing loss, and so on. In addition, it is advantageous to meet the requirements on quantitative use and sterilization of microcarriers in a cell culture process.

The "cell carrier particle" as described in the present disclosure refers to a microcarrier with a diameter of 1 to 1000 um prepared from a synthetic polymers and/or a natural biopolymers. The synthetic polymer is at least one selected from the group comprising polyethylene glycol, polyethylene glycol derivatives, polyethylene glycol diacrylate (PEGDA4000), polypropylene, polystyrene, polyacrylamide, polylactic acid, poly(hydroxy acid), poly(lactic-co-glycolic acid), polydimethylsiloxane, polyanhydride, poly(acid ester), polyamide, poly(amino acid), polyacetal, polycyanoacrylate, polyurethane, polypyrrole, polyester, polymethacrylate, polyethylene, polycarbonate, and polyethylene oxide. The natural biopolymer is at least one selected from the group comprising collagen, proteoglycan, glycoprotein, gelatin, gelatin derivatives, alginate, alginate derivatives, agar, matrigel, hyaluronic acid, laminin, fibronectin, or tissue decellularized materials.

The cell carrier particle aggregate provided by the present disclosure is formed by aggregating cell carrier particles and has a particular shape. The particular shape includes the shape of a tablet and the shape of a block. The tablet or the block may have a cross section that is circular, cylindrical, square, diamond-shaped, triangular, oval, concave or convex polygonal, etc. The aggregate of cell carrier particles has an excellent rehydration property and a good dispersibility upon rehydration.

The aggregate of cell carrier particles according to the present disclosure may be prepared by the following method: aggregating and shaping cell carrier particles under an external force to obtain the aggregate of cell carrier particles.

Specifically, the cell carrier particles can be aggregated and shaped by a punch-forming process.

The punch-forming process is performed under the following conditions:
  a punch mold is selected from a beveled flat punching mold, a shallow arc punching mold, a deep arc punching mold, or a full flat punching mold;
  a punch-forming machine has an upper punch with an adjusting range between 0 and 50 mm, and a lower punch with an adjusting range between 0 and 50 mm;
  a pressure ranges from 0 to 200 KN, which can be selected according to practical need in order to prepare an aggregate of cell carrier particles with a suitable hardness; and
  specifically, an automatic punch-forming machine may be used, with each tablet of the aggregate of cell carrier particles be automatically obtained after a rotation of the motor rocker.

For a punch-forming machine, the mass and weight of a material are determined by measuring the volume thereof.

Specifically, the cell carrier particles can be aggregated and shaped by a mold-forming process.

The mold-forming process comprises the following steps of:
  mixing the cell carrier particles with water or a volatile organic solvent and filling the resultant mixture into a mold; and then placing the mold in an oven and drying to obtain the aggregate of cell carrier particles;
  wherein the water or the organic solvent may be added in an amount of 5 to 100 times of the mass of the cell carrier particles;
  the organic solvent may be a solvent such as methanol, ethanol, tert-butanol, or isopropanol; and
  the temperature of the oven may be 30-200° C., and the drying may be performed for a period of 12-96 hours; as such, a firm and stable aggregate of cell carrier particles with an uniform unit mass and the same shape can be obtained.

Specifically, the cell carrier particles can be aggregated and shaped by a lyophilization process.

The lyophilization process comprises the following steps of:
  mixing the cell carrier particles with water or a volatile organic solvent and shaping the resultant mixture into a particular shape, followed by freezing the shaped mixture to obtain a frozen mixture; and lyophilizing the frozen mixture to obtain the aggregate of cell carrier particles;
  wherein the water or the organic solvent may be added in an amount of 5 to 100 times of the mass of the cell carrier particles;
  the organic solvent may be a solvent such as methanol, ethanol, tert-butanol, or isopropanol solvent;
  the shaped mixture is frozen in a freezing container at a low temperature ranging from −196° C. to 0° C. to obtain the frozen mixture; and
  the frozen mixture is lyophilized in a lyophilizer for 2 to 96 hours to obtain the aggregate of cell carrier particles.

Specifically, the cell carrier particles can be aggregated and shaped by a dehydrating-evaporating process;
  wherein the dehydrating-evaporating process comprises the following steps of:
  mixing the cell carrier particles with water or a volatile organic solvent and shaping the mixture into a particular shape; and then dehydrating and evaporating the shaped mixture to obtain the aggregate of cell carrier particles;
  wherein the water or the organic solvent may be added in an amount of 5 to 100 times of the mass of the cell carrier particles;
  the organic solvent may be a solvent such as methanol, ethanol, tert-butanol, or isopropanol solvent;
  by using natural dehydration at room temperature, such as volatilization at room temperature for 1 to 7 days, a firm and stable aggregate of cell carrier particles with a regular shape can be obtained; and
  by using drying in an oven, for example, by drying in an oven for 2 to 96 hours, a firm and stable aggregate of cell carrier particles with a regular shape can be obtained.

BRIEF DESCRIPTION OF THE DRAWINGS

The present disclosure will hereinafter be described in conjunction with the following drawing figures, wherein like numerals denote like elements, and.

DETAILED DESCRIPTION

Figure 1:
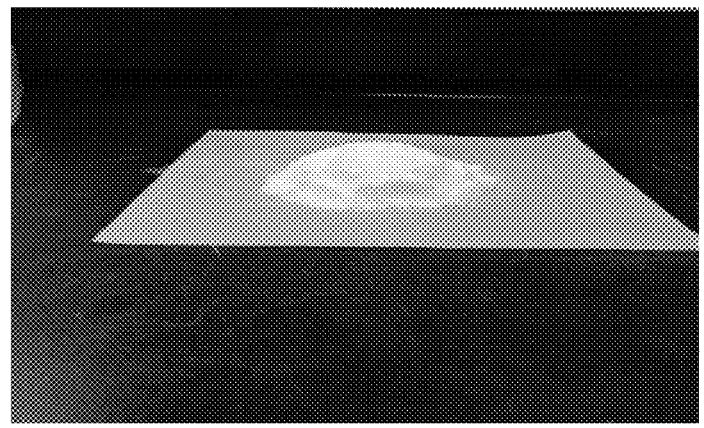
FIG. 1 is a photograph of the cell carrier particles in Example 1 of the present disclosure.

The following detailed description is merely exemplary in nature and is not intended to limit the disclosure or the application and uses of the disclosure. Furthermore, there is no intention to be bound by any theory presented in the preceding background of the disclosure or the following detailed description.

EXAMPLES

Unless otherwise specified, the experimental methods used in the following examples are conventional methods.

Unless otherwise specified, the materials, reagents and the like used in the following examples are all available from market.

The individual cell carrier particles used in the following examples 1-4 were prepared as followed.

Preparation of a reaction solution: PEGDA4000 powder was dissolved in a DPBS solution at room temperature to obtain a pre-polymerized solution; the pre-polymerized solution was then mixed adequately with ammonium persulfate and N,N,N',N'-tetramethyl ethylenediamine to obtain a reaction solution, wherein the concentration of PEGDA4000 in the reaction solution was 10 g/100 ml, the concentration of ammonium persulfate in the reaction solution was 0.5 g/100 ml, and the concentration of N,N,N',N'-tetramethyl ethylenediamine in the reaction solution was 0.05 g/100 ml.

Preparation of individual cell carrier particles with an arrayed mold: a PMMA mold with apertures in an array format, which was already prepared, was placed in an ice bath, 200 ul of the prepared reaction solution was added dropwise on the PMMA mold uniformly, and then the reaction solution on the surface of the mold was slowly and evenly scraped into the pores in the mold by using a cover glass. The mold filled with the PEGDA reaction solution was frozen at −20° C. for 20 hours. After the reaction was finished, the mold was transferred into a lyophilizer (−50° C., 20 pa) and dried for 30 minutes to obtain white porous cell carrier particles with a diameter of 1-1000 um.

Example 1. Punch-Forming Process

The punch-forming machine is an automatic punch-forming machine, with a tablet of product obtained after a rotation of the motor rocker. For the punch-forming machine, the mass and weight of a material were determined by measuring the volume thereof.

20 mg cell carrier particles were first weighed on a balance, the weighed material was then poured into the feed port of the punch-forming machine, and a beveled flat punching mold was selected. The upper punch of the punch-forming machine was adjusted in a range from 0 to 50 mm, and the lower punch of the punch-forming machine was adjusted in a range from 0 to 50 mm. The handle of the punch-forming machine was run to fill up the mold with the material and the pressure was adjusted in a range from 0 to 200 KN. The motor was turned on, and, one punch-forming operation was finished after one rotation of the motor rocker. The automatic punch-forming machine can continuously perform the punch forming operation at a constant speed, wherein the punch-forming rate was 1 to 10 seconds per tablet. After the punch-forming process was finished, the aggregates were placed in a container prepared in advance.

Figure 2:
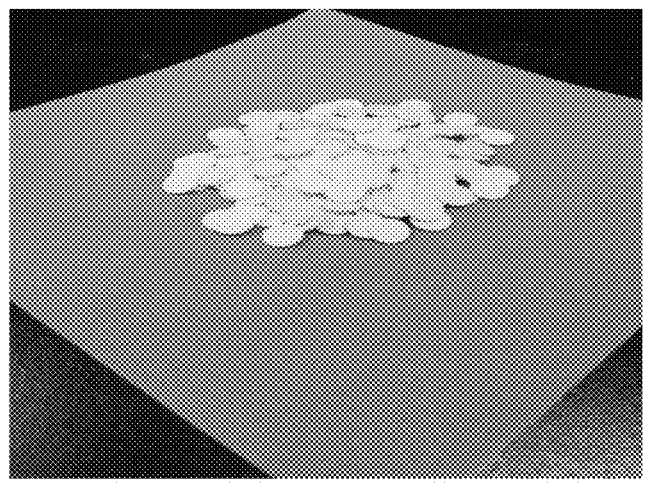
FIG. 2 is a photograph of the punch-formed cell carrier particles in Example 1 of the present disclosure.

The photograph of the aggregates formed in this example is shown in FIG. 2, and FIG. 1 is a photograph of the powdery cell carrier particles before the forming process.

In the method of this example, the unit mass of the aggregate can be controlled by adjusting the height of the lower punch, that is, by adjusting the volume of the material.

During the above preparation process, attention needs to be paid to the following operations:

(1) when performing the punch-forming operation, the punch-forming strength should be increased (by adjusting the height of the upper punch, the punch-forming strength may be increased; here turn left to lower the height and turn right to increase the height) to compact the tablets, so that the aggregated tablets would not be broken up by a small impact;

(2) when adjusting the mass of the tablet-like aggregates, the rocker must be kept perpendicular to the horizontal plane with 90° upward;

(3) when performing the punch-forming operation, it should be observed whether the mold has been filled up with the material; if not, it needs to rotate the handle in a backward direction and to fill up the mold with the material, so as to ensure that the mass of every tablet is accurate; and (4) because for the punch-forming machine, the mass of the material is determined by measuring the volume thereof, it needs to change the mold in order to obtain products with a desired mass by the punch-forming process. The mass can be controlled within a range between 1 mg to 1000 mg.

The aggregates prepared in this example were placed in a container and the container was then placed on a shaker under continuous shaking. The rotation speed of the shaker was in the range of 0 to 1000 rpm, and the aggregates were found to be not friable or the like even after continuous shaking for 96 hours. It can be seen that the aggregates prepared in this example are stable in shape and not easy to be broken up, and the unit mass is accurate and adjustable.

Figure 3:
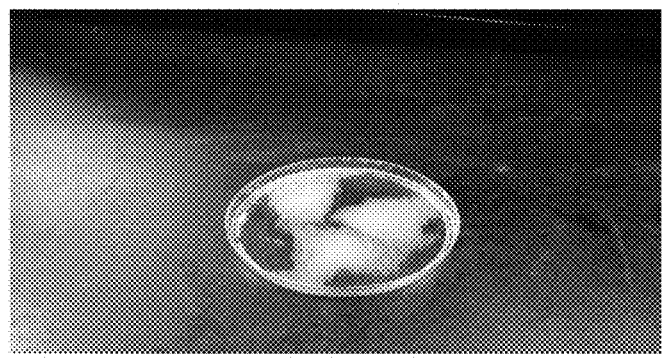
FIG. 3 shows the initial state of the aggregate of cell carrier particles when being dispersed in the liquid in Example 1 of the present disclosure.
Figure 4:
FIG. 4 shows the final state of the aggregate of cell carrier particles after being completely dispersed in the liquid in Example 1 of the present disclosure.
Figure 5:
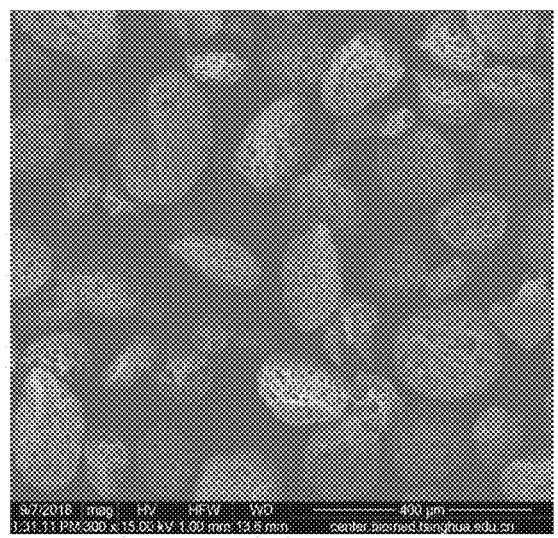
FIG. 5 is an SEM photograph of the cell carrier particles in Example 1 of the present disclosure.
Figure 6:
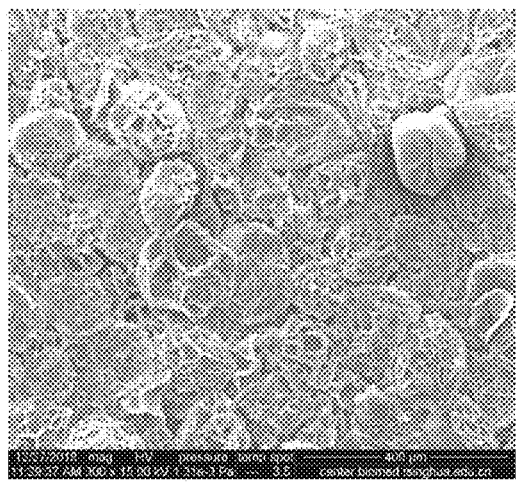
FIG. 6 is an SEM photograph of the aggregate of cell carrier particles in Example 1 of the present disclosure.
Figure 7:
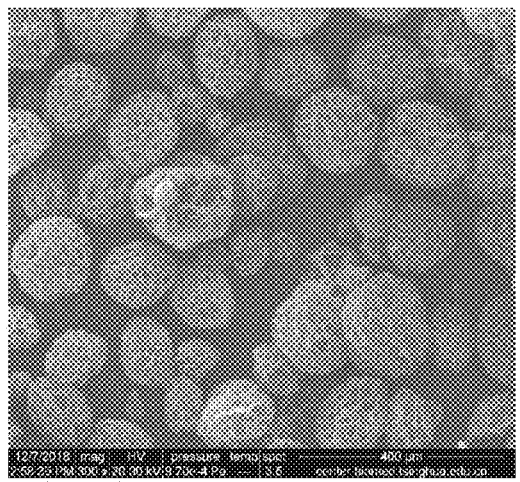
FIG. 7 is an SEM photograph of the particles obtained after dispersing the aggregate of cell carrier particles in the liquid in Example 1 of the present disclosure.

After the addition of a very small amount of liquid to the aggregates prepared in this example, the aggregates were rapidly dispersed to form separate carrier supports without any change in physical and chemical properties. FIG. 3 shows the initial state of the aggregates when being dispersed in the liquid, and FIG. 4 shows the final state of the aggregates after being completely dispersed in the liquid. FIG. 5 is an SEM photograph of the cell carrier particles before the punch-forming process; FIG. 6 is an SEM photograph of the aggregates of cell carrier particles after the punch-forming process; FIG. 7 is an SEM photograph of the powdery cell carrier particles after the punch-forming process, dispersion in the liquid, and lyophilization. By comparison of the SEM photographs representing the three states, it can be seen that after the punch-forming process, the cell carrier particles still maintained their properties, such as spherical appearance, porous connectivity, and dispersibility as compared with those prior to the punch-forming process, which would be advantageous for the subsequent adherent cell culture.

The aggregates of cell carrier particles prepared in this example are convenient for packaging and transportation, and avoid the static electricity resulted from powdery products and the loss caused thereby. The aggregates can be individually packaged and sterilized, which is convenient for the aseptic operations in cell culture. In addition, the aggregates can be quantitatively shaped and therefore are convenient for use.

Example 2. Mold-Forming Process

Figure 8:
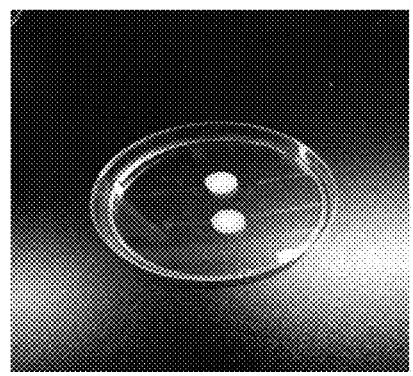
FIG. 8 is a photograph showing the cell carrier particles being filled into cylindrical aggregation molds in Example 2 of the present disclosure.
Figure 9:
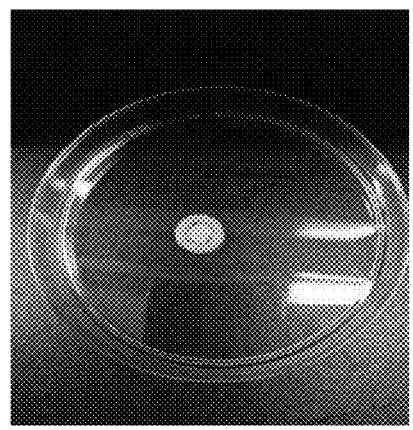
FIG. 9 is a photograph of the mold-formed cell carrier particles in Example 2 of the present disclosure.

To a certain amount of powdery cell carrier particles, deionized water was added in an amount of 50 times of the weight of the cell microcarriers. By using auxiliary tools, the mold was filled up with the resultant mixture evenly. The mold was cylindrical (which may also be circular, square, diamond-shaped, triangular, oval, or concave or convex polygonal, etc.). The mold containing a certain amount of cell carrier particles (as shown in FIG. 8) was placed in an oven at 60° C. and dried continuously for 96 hours to obtain firm and stable aggregates of cell carrier particles with an uniform unit mass and the same shape, as shown in FIG. 9.

Figure 10:
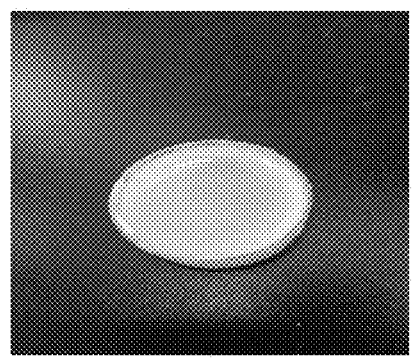
FIG. 10 is a photograph of the aggregate of cell carrier particles after being dispersed in the liquid in Example 2 of the present disclosure.

When the aggregates of cell carrier particles prepared in this example were added to water, the aggregates could be rapidly dispersed to form separate cell carrier particles, as shown in FIG. 10. This result shows that the appearance and physical properties of the particles were kept unchanged.

The aggregates of cell carrier particles prepared in this example can quickly absorb water and be dispersed after contacting the liquid, which would be advantageous for the subsequent adherent cell culture.

After comparison of the SEM photographs of cell carrier particles before and after the forming process, as well as after rehydration and dispersion in the liquid, it can be seen that the cell carrier particles after the mold-forming process in this example had maintained their properties such as spherical appearance, porous connectivity, and dispersibility as compared with those prior to the punch-forming process.

The aggregates of cell carrier particles prepared in this example are convenient for packaging and transportation, and avoid the static electricity resulted from powdery products and the loss caused thereby. The aggregates can be individually packaged and sterilized, which is convenient for the aseptic operations in cell culture. In addition, the aggregates can be quantitatively shaped and therefore are convenient for use.

Example 3. Lyophilization Forming Process

Figure 11:
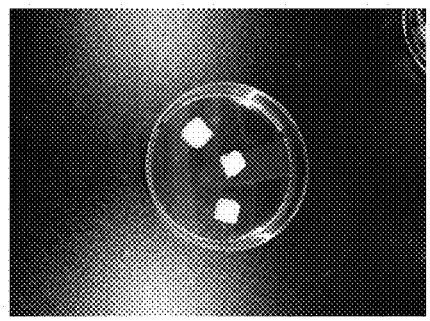
FIG. 11 is a photograph of the cell carrier particles aggregated after absorbing water in Example 3 of the present disclosure.
Figure 12:
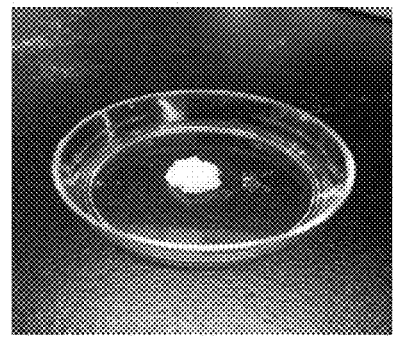
FIG. 12 is a photograph of the lyophilization-formed cell carrier particles in Example 3 of the present disclosure.

To a certain amount of powdery microcarriers, deionized water was added in an amount of 100 times of the weight of the cell microcarriers. By using auxiliary tools, the resultant mixture was aggregated into blocks with a regular shape, as shown in FIG. 11. The aggregates were frozen in a freezing container at a low temperature ranging from −196° C. to 0° C. to form frozen blocks. The frozen aggregates were lyophilized in a lyophilizer for 96 hours; after being taking out, lyophilized aggregates were formed, as shown in FIG. 12.

Figure 13:
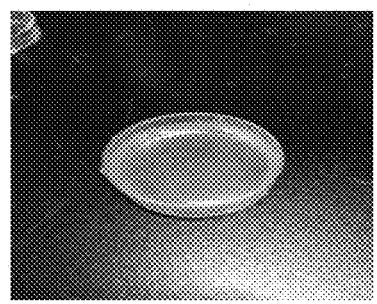
FIG. 13 is a photograph of the aggregate of cell carrier particles after being dispersed in the liquid in Example 3 of the present disclosure.

When the aggregates of cell carrier particles prepared in this example were added to water, the aggregates were rapidly dispersed to form separate microcarrier particles, as shown in FIG. 13. This result shows that the appearance and physical properties of the particles were kept unchanged.

The aggregates of cell carrier particles prepared in this example can quickly absorb water and be dispersed after contacting the liquid, which would be advantageous for the subsequent adherent cell culture.

After comparison of the SEM photographs of the cell carrier particles before and after the forming process, as well as after rehydration and dispersion in the liquid, it can be seen that the cell carrier particles after the lyophilization forming process in this example had maintained their properties such as spherical appearance, porous connectivity, and dispersibility as compared with those prior to the punch-forming process.

The aggregates of cell carrier particles prepared in this example are convenient for packaging and transportation, and avoid the static electricity resulted from powdery products and the loss caused thereby. The aggregates can be individually packaged and sterilized, which is convenient for the aseptic operations in cell culture. In addition, the aggregates can be quantitatively shaped and therefore are convenient for use.

Example 4. Dehydrating-Evaporating Forming Process

Figure 14:
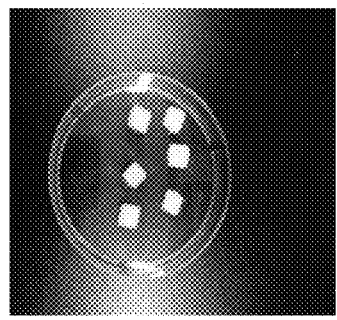
FIG. 14 is a photograph of the cell carrier particles aggregated after absorbing water in Example 4 of the present disclosure.
Figure 15:
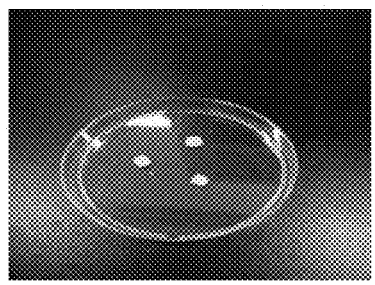
FIG. 15 is a photograph of the cell carrier particles formed after a dehydrating-evaporating process in Example 4 of the present disclosure.

To a certain amount of powdery microcarriers, deionized water was added in an amount of 20 times of the weight of the cell microcarriers. By using auxiliary tools, the resultant mixture formed blocks with a regular shape, as shown in FIG. 14. The cell microcarrier blocks with a certain mass were naturally dehydrated and evaporated at room temperature. After volatilization for 7 days, firm and stable cell microcarrier aggregates with a regular shape were obtained, as shown in FIG. 15.

Figure 16:
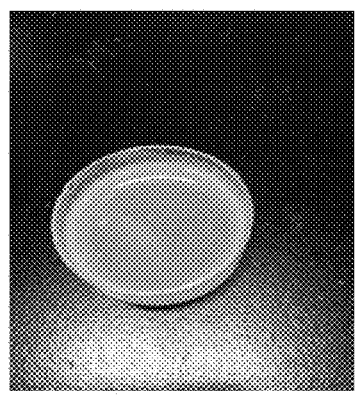
FIG. 16 is a photograph of the aggregate of cell carrier particles after being dispersed in a liquid in Example 4 of the present disclosure.

When the aggregates of cell carrier particles prepared in this example were put into water, the aggregates were rapidly dispersed to form separated microcarrier particles, as shown in FIG. 16. This result shows that the appearance and physical properties of the particles were kept unchanged.

The aggregates of cell carrier particles prepared in this example can quickly absorb water and be dispersed after contacting the liquid, which would be advantageous for the subsequent adherent cell culture.

After comparison of the SEM photographs of the cell carrier particles before and after the forming process, as well as after rehydration and dispersion, it can be seen that the cell carrier particles after the dehydrating-evaporating forming process in this example had maintained their properties such as spherical appearance, porous connectivity, and dispersibility as compared with those prior to the punch-forming process The aggregates of cell carrier particles prepared in this example are convenient for packaging and transportation, and avoid the static electricity resulted from powdery products and the loss caused thereby. The aggregates can be individually packaged and sterilized, which is convenient for the aseptic operations in cell culture. In addition, the aggregates can be quantitatively shaped and therefore are convenient for use.

Example 5. Aggregates of Gelatin Cell Carrier Particles

Preparation of a reaction solution: Gelatin powder was dissolved in water at 60° C. to a 7% solution, and then incubated on ice for 30 min. To each mL of 7% gelatin solution, 70 μL of 0.5% glutaraldehyde was added and mixed thoroughly to form the reaction solution.

Figure 17:
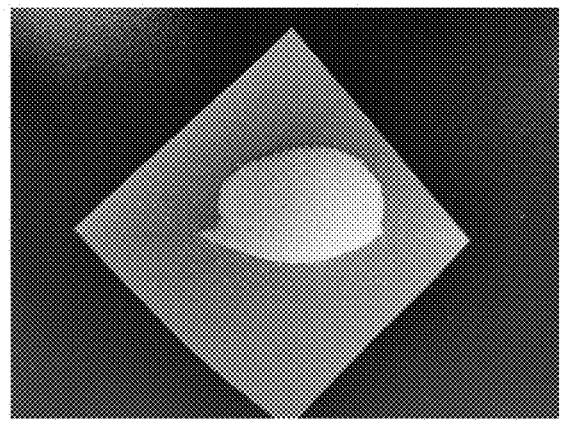
FIG. 17 is a photograph of individual gelatin porous cell carrier particles before aggregation.

Preparation of individual cell carrier particles with an arrayed mold: a PMMA mold with apertures in an array format, which was already prepared, was placed in an ice bath, 200 μl of the prepared reaction solution was added dropwise on the PMMA mold uniformly, and then the reaction solution on the surface of the mold was slowly and evenly scraped into the pores in the mold by using a cover glass. The mold filled with the gelatin reaction solution was frozen at −20° C. for 16 hours. After the reaction was finished, the mold was transferred into a lyophilizer (−50° C., 20 Pa) and dried for 30 minutes to obtain white porous cell carrier particles (FIG. 17).

Figure 18:
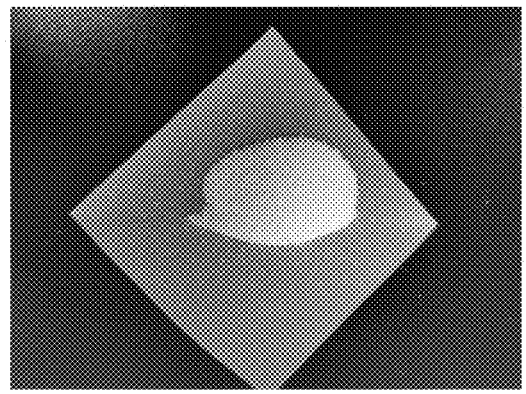
FIG. 18 is a photograph of gelatin porous cell carrier aggregates remain intact after shaking at 60 rpm on an orbital shaker.

Preparation of aggregates of cell carrier particles: 20 mg of gelatin cell carrier particles were first weighed on a balance, the weighed material was then poured into the feed port of the punch-forming machine, and a beveled flat punching mold was selected. The upper punch of the punch-forming machine was adjusted in a range from 0 to 50 mm, and the lower punch of the punch-forming machine was adjusted in a range from 0 to 50 mm. The handle of the punch-forming machine was run to fill up the mold with the material and the pressure was adjusted in a range from 0 to 200 KN. The motor was turned on, and, one punch-forming operation was finished after one rotation of the motor rocker. The automatic punch-forming machine can continuously perform the punch forming operation at a constant speed, wherein the punch-forming rate was 1 to 10 seconds per tablet. After the punch-forming process was finished, the aggregates were placed in a container and underwent a stability test where the container containing the aggregates were placed on an orbital shaker operating at 60 rpm. The aggregates remained intact as shown in FIG. 18.

Figure 19:
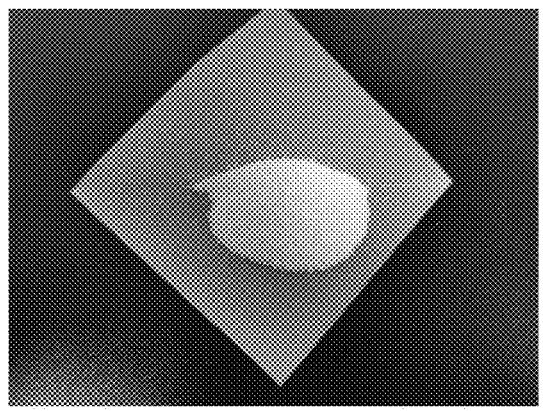
FIG. 19 is a photograph of initial dispersion state of gelatin porous cell carrier aggregates upon addition of fluid.
Figure 20:
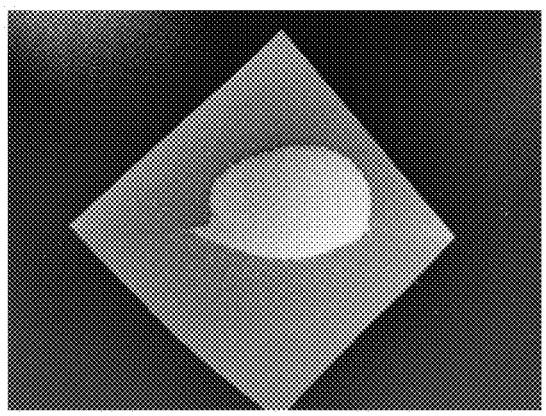
FIG. 20 is a photograph of gelatin porous cell carrier aggregates fully dispersed in fluid.
Figure 21:
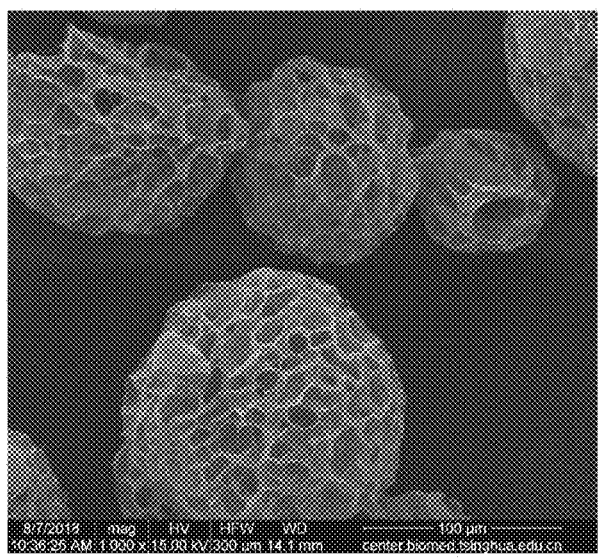
FIG. 21 is a photograph of SEM image of individual gelatin porous cell carrier particles before aggregation.

After the addition of a small amount of liquid to the aggregates prepared in this example, the aggregates were rapidly dispersed to form separate carrier supports without any change in physical and chemical properties. FIG. 19 shows the initial state of the aggregates when being dispersed in the liquid, and FIG. 20 shows the final state of the aggregates after being completely dispersed in the liquid. FIG. 21 is an SEM photograph of the cell carrier particles before the punch-forming process.

Example 6. Aggregates of Gelatin-Fibronectin Cell Carrier Particles

Preparation of a reaction solution: Gelatin powder was dissolved in water at 60° C. to a 10% solution, and then incubated on ice for 30 min. Fibronectin was prepared as a 2% solution in water at room temperature. Mix the fibronectin solution with gelatin solution at 1:1 ratio to form a mixed solution of gelatin and fibronectin at a concentration of 5% and 1% respectively. To each mL of 7% the mixed solution, 70 µL of 0.5% glutaraldehyde was added and mixed thoroughly to form the reaction solution.

Figure 22:
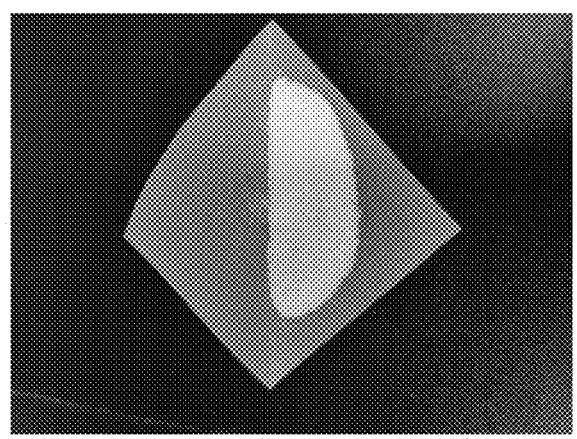
FIG. 22 is a photograph of individual gelatin-fibronectin porous cell carrier particles before aggregation.

Preparation of individual cell carrier particles with an arrayed mold: a PMMA mold with apertures in an array format, which was already prepared, was placed in an ice bath, 200 µl of the prepared reaction solution was added dropwise on the PMMA mold uniformly, and then the reaction solution on the surface of the mold was slowly and evenly scraped into the pores in the mold by using a cover glass. The mold filled with the gelatin reaction solution was frozen at −20° C. for 16 hours. After the reaction was finished, the mold was transferred into a lyophilizer (−50° C., 20 Pa) and dried for 30 minutes to obtain white porous cell carrier particles (FIG. 22).

Figure 23:
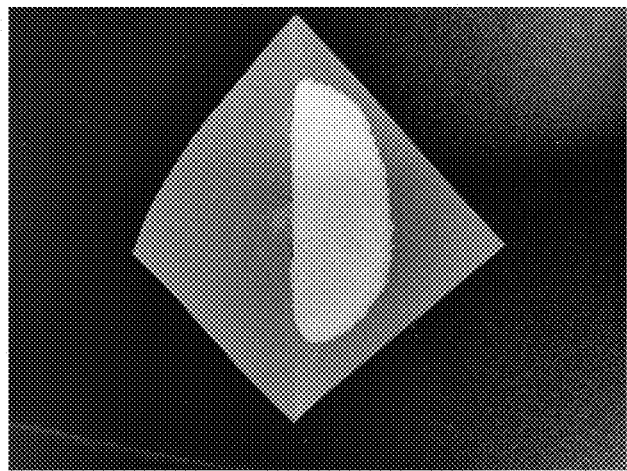
FIG. 23 is a photograph of gelatin-fibronectin porous cell carrier aggregates remain intact after shaking at 60 rpm on an orbital shaker.

Preparation of aggregates of cell carrier particles: 20 mg of gelatin cell carrier particles were first weighed on a balance, the weighed material was then poured into the feed port of the punch-forming machine, and a beveled flat punching mold was selected. The upper punch of the punch-forming machine was adjusted in a range from 0 to 50 mm, and the lower punch of the punch-forming machine was adjusted in a range from 0 to 50 mm. The handle of the punch-forming machine was run to fill up the mold with the material and the pressure was adjusted in a range from 0 to 200 KN. The motor was turned on, and, one punch-forming operation was finished after one rotation of the motor rocker. The automatic punch-forming machine can continuously perform the punch forming operation at a constant speed, wherein the punch-forming rate was 1 to 10 seconds per tablet. After the punch-forming process was finished, the aggregates were placed in a container and underwent a stability test where the container containing the aggregates were placed on an orbital shaker operating at 60 rpm. The aggregates remained intact as shown in FIG. 23.

Figure 24:
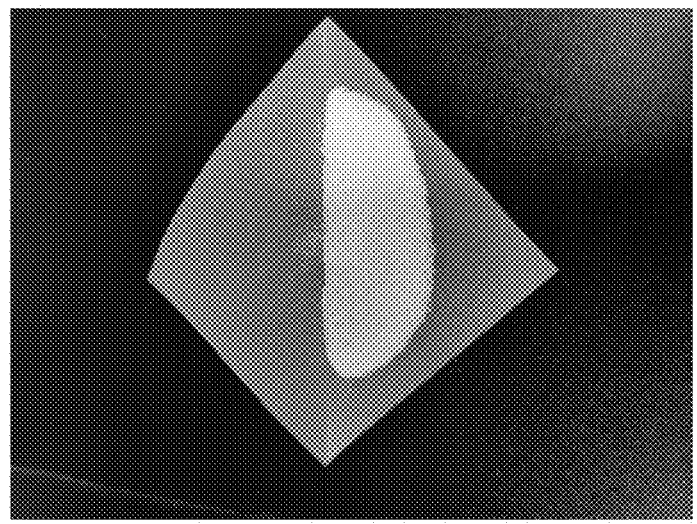
FIG. 24 is a photograph of gelatin-fibronectin porous cell carrier aggregates fully dispersed in fluid.
Figure 25:
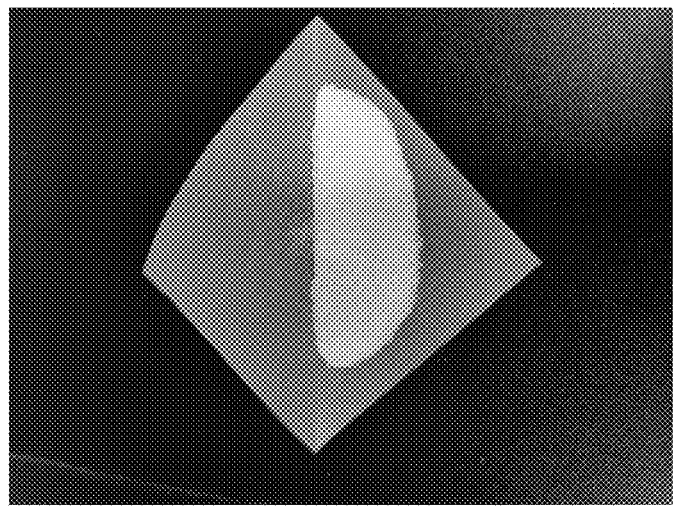
FIG. 25 is a photograph of gelatin-fibronectin porous cell carrier aggregates fully dispersed into individual particles in fluid when viewed under microscope.
Figure 26:
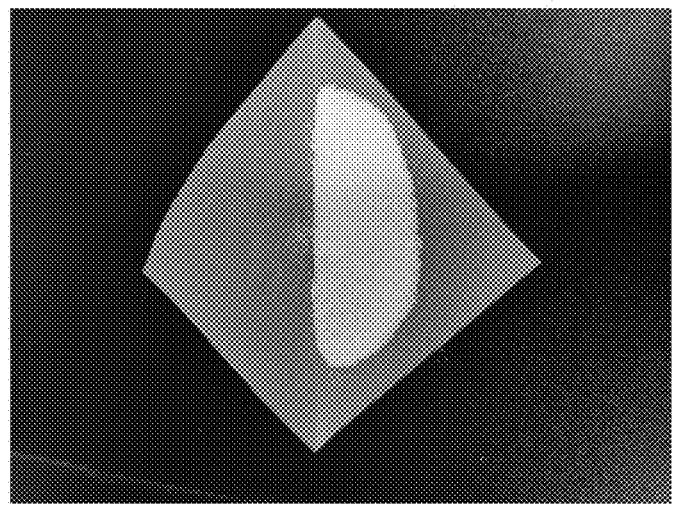
FIG. 26 is a photograph of SEM image of individual gelatin-fibronectin porous cell carrier particles before aggregation.

After the addition of a small amount of liquid to the aggregates prepared in this example, the aggregates were rapidly dispersed to form separate carrier supports without any change in physical and chemical properties. FIG. 24 shows the aggregates when fully dispersed in the liquid, and FIG. 25 shows the dispersed cell carrier particles when observed under a typical microscope. FIG. 26 is an SEM photograph of the cell carrier particles before the punch-forming process.

INDUSTRIAL APPLICATIONS

The present disclosure achieves the following beneficial effects.

In the aggregates of cell carrier particles according to the present disclosure, the cell carrier particles have a porous connectivity, and have great elasticity and resistance to extrusion. After pressing carrier particles into aggregates, these carrier particles can be rapidly dispersed into separate carrier supports by adding a very small amount of liquid, without any change in physical and chemical properties. After comparison of the SEM photographs of the cell carriers in a powder form before the aggregating and shaping step, the cell carriers after being aggregated into tablet-like aggregates, and the cell carriers after the lyophilized aggregates absorbed water and were dispersed, it can be seen that the cell carrier particles after the punch-forming process had maintained their properties in spherical appearance, porous connectivity, and dispersibility as compared with those prior to the punch-forming process, which would be advantageous for the subsequent adherent cell culture. Therefore, the aggregate of cell carrier particles according to the present disclosure has an extremely strong rehydration property and a good dispersibility upon rehydration, and the physical properties of the cell carrier particles remain unchanged before and after aggregation.

Since there is no loose powder on the surface of the aggregates obtained by the forming processes without adding other ingredients, the static electricity is reduced as much as possible. The products are aesthetic and convenient for use, thereby avoiding the static electricity resulted from powdery products and the loss caused thereby.

The aggregate of cell carrier particles according to the present disclosure can be quantified, sterilized and stored in the form of a single tablet in a medicine blister packaging, or can be quantified, sterilized and stored in the form of multiple tablets in a vial. Such individual packaging and sterilization would be convenient for the aseptic operations in cell culture.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An aggregate of cell carrier particles, wherein the aggregate of cell carrier particles is formed by aggregating cell carrier particles, wherein the aggregate of cell carrier particles is in a dehydrated state and can be rehydrated to form separate microcarrier particles dispersed in water,
   wherein the aggregate of cell carrier particles is formed by a punch-forming process, mold-forming process, lyophilization process or dehydrating-evaporating forming process, and
   wherein the aggregate of cell carrier particles does not include other ingredients than the cell carrier particles.

2. The aggregate of cell carrier particles according to claim 1, further comprising the aggregate of cell carrier particles having a particular shape.

3. The aggregate of cell carrier particles according to claim 2, wherein the particular shape further comprises the shape of a tablet or a block.

4. A method for preparing the aggregate of cell carrier particles of claim 1, comprising:
aggregating and shaping cell carrier particles under an external force to obtain the aggregate of cell carrier particles,
the method further comprising performing the punch-forming process under the following conditions:
a punching mold is selected from a beveled flat punching mold, a shallow arc punching mold, a deep arc punching mold, or a full flat punching mold;
a punch-forming machine has an upper punch with an adjusting range between 0 and 50 mm, and a lower punch with an adjusting range between 0 and 50 mm; and
a pressure ranges from 0 to 200 KN.

5. A method for preparing the aggregate of cell carrier particles of claim 1, comprising:
aggregating and shaping cell carrier particles under an external force to obtain the aggregate of cell carrier particles,
wherein the mold-forming process comprises the following steps of:
mixing the cell carrier particles with water or a volatile organic solvent and filling the resultant mixture into a mold; and then placing the mold in an oven and drying to obtain the aggregate of cell carrier particles.

6. The method according to claim 5, further comprising the water or the organic solvent is added in an amount of 5 to 100 times of the mass of the cell carrier particles; and
the temperature of the oven is 30 to 200° C., and the drying is performed for a period of 12 to 96 hours.

7. A method for preparing the aggregate of cell carrier particles of claim 1, comprising:
aggregating and shaping cell carrier particles under an external force to obtain the aggregate of cell carrier particles,
wherein the lyophilization process comprises the following steps of:
mixing the cell carrier particles with water or a volatile organic solvent and shaping the resultant mixture into a particular shape, followed by freezing the shaped mixture to obtain a frozen mixture; and lyophilizing the frozen mixture to obtain the aggregate of cell carrier particles.

8. The method according to claim 7, wherein the water or the organic solvent is added in an amount of 5 to 100 times of the mass of the cell carrier particles;
the shaped mixture is frozen in a freezing container at a low temperature ranging from −196° C. to 0° C. to obtain the frozen mixture; and
the frozen mixture is lyophilized in a lyophilizer for a period of 2 to 96 hours to obtain the aggregate of cell carrier particles.

9. A method for preparing the aggregate of cell carrier particles of claim 1, comprising:
aggregating and shaping cell carrier particles under an external force to obtain the aggregate of cell carrier particles,
wherein the dehydrating-evaporating forming process comprises the following steps of:
mixing the cell carrier particles with water or a volatile organic solvent and shaping the mixture into a particular shape; and then dehydrating and evaporating the shaped mixture to obtain the aggregate of cell carrier particles.

10. The method according to claim 9, characterized in that the water or the organic solvent is added in an amount of 5 to 100 times of the mass of the cell carrier particles.

11. The method according to claim 10, wherein the cell carrier particles are aggregated and shaped by natural dehydration at room temperature.

12. The method according to claim 10, wherein the cell carrier particles are aggregated and shaped by drying in an oven.

* * * * *